United States Patent [19]

Materne

[11] 4,364,952
[45] Dec. 21, 1982

[54] CERTAIN 1,4-DIHYDRO-2,6-DIMETHYL-3,5-PYRIDINE-DICARBOXYLATES, COMPOSITION CONTAINING SAME AND METHOD OF USE

[75] Inventor: Carsten Materne, Bonn, Fed. Rep. of Germany

[73] Assignee: Bayer Aktiengesellschaft, Leverkusen, Fed. Rep. of Germany

[21] Appl. No.: 268,417

[22] Filed: May 29, 1981

[30] Foreign Application Priority Data

Jun. 12, 1980 [DE] Fed. Rep. of Germany ....... 3021958

[51] Int. Cl.$^3$ .................. A61K 31/455; C07D 213/55
[52] U.S. Cl. ..................................... 424/266; 546/321
[58] Field of Search ......................... 546/321; 424/266

[56] References Cited

U.S. PATENT DOCUMENTS 3,485,847 12/1969 Bossert et al. ...................... 546/321
4,048,171 9/1977 Bossert et al. ...................... 546/321

*Primary Examiner*—Alan L. Rotman
*Attorney, Agent, or Firm*—Sprung, Horn, Kramer & Woods

[57] ABSTRACT

The invention relates to 1,4-dihydropyridines which carry an arylalkyl or aryloxyalkyl radical in the 4-position. Also included in the invention are methods for the preparation of said compounds. The invention further relates to compositions containing said 1,4-dihydropyridines and the use of said compounds and compositions for their circulation influencing effects.

9 Claims, No Drawings

CERTAIN 1,4-DIHYDRO-2,6-DIMETHYL-3,5-PYRIDINE-DICARBOXYLATES, COMPOSITION CONTAINING SAME AND METHOD OF USE

The present invention relates to certain new 1,4-dihydropyridine compounds, to processes for their production and to their use as medicaments for influencing the circulation.

It is already known that 1,4-dihydropyridine derivatives have circulation-influencing properties. Thus for example, 2,6-dimethyl-4-(2'-nitrophenyl)-1,4-dihydropyridine-3,5-dicarboxylic acid dimethyl ester, a compound known under the Trade Mark "Nifedipin", (see German Patent Specification No. 1,607,827) is known as a compound which has a coronary-vasodilating action.

According to the present invention there are provided compounds which are 1,4-dihydropyridines of the formula

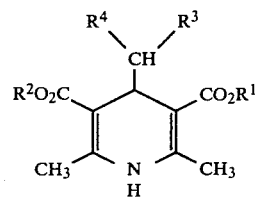

or a salt thereof, in which
  $R^1$ and $R^2$ are identical or different and denote a straight-chain or branched alkyl radical with 1 to 4 carbon atoms,
  $R^3$ denotes a hydrogen atom, a methyl group or a phenyl radical and
  $R^4$ represents a phenyl or phenoxy radical, which optionally carry 1 or more substituents selected from nitro, halogen, methyl and methoxy.

1,4-Dihydropyridines which carry an arylalkyl or aryloxyalkyl radical in the 4-position have not previously been described.

The compounds of the present invention possess circulation-influencing properties, and in particular dilate the coronary vessels and lower the blood pressure.

According to the present invention there is further provided a process for the production of compounds of the invention in which
  (a) an aldehyde of the formula

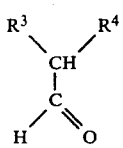

in which $R^3$ and $R^4$ have the abovementioned meaning, is reacted with ammonia and an acetoacetic acid ester of the formula

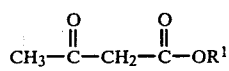

in which $R^1$ has the abovementioned meaning, in an organic solvent, (b) an aldehyde of formula (II), as defined above, is reacted with an enamino-ester of the formula

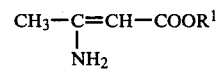

in which $R^1$ has the abovementioned meaning, in an organic solvent, or
  (c) an ylidene compound of the formula

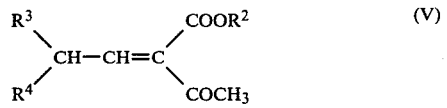

in which $R^2$, $R^3$ and $R^4$ have the abovementioned meanings, is reacted with an enamino-ester of the formula (IV), as defined above, in an organic solvent.

The organic solvent used can be an alcohol (especially an alkanol having 1 to 4 carbonatous, particularly methanol, ethanol and isopropanol), dioxane, glacial acetic acid, ethyl acetate, dimethylformamide or acetonitrile. The reaction temperatures can be varied over a wide range, preferably between 20° C. and 150° C. More preferably, the reaction is carried out at the boiling point of the solvent.

The starting materials which can be used are mostly known compounds, or can be prepared in accordance with known processes.

As examples of aldehydes of the formula (II) there can be mentioned: 2-(3-methoxyphenyl)-propionaldehyde, 2-(4'-methoxyphenyl)-propionaldehyde, 2-(3',4'-dimethoxyphenyl)-propionaldehyde, 3,4-dimethoxyphenylacetaldehyde, 2-(4'-chlorophenyl)-propionaldehyde, 2-(2'-chlorophenyl)propionaldehyde, 2-chlorophenylacetaldehyde, 4-chlorophenylacetaldehyde, 2-(3-nitrophenyl)-propionaldehyde, diphenylacetaldehyde, 2,6-dimethoxyphenoxyacetaldehyde and 2,6-dichlorophenoxyacetaldehyde.

Examples of acetoacetic acid esters of formula (III) suitable for use in reaction variant (a) are methyl acetoacetate, ethyl acetoacetate, propyl acetoacetate, isopropyl acetoacetate, butyl acetoacetate, sec.-butyl acetoacetate and isobutyl acetoacetate.

The enamino esters of the formula (IV), suitable for use in reaction variant (b), are obtained from the corresponding acetoacetic acid esters of the formula (III) by reaction with ammonia.

As stated above, the invention also relates to the use in medicine as circulation-influencing agents of the compounds of the invention.

The present invention provides pharmaceutical compositions containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally.

Administration according to the invention is preferably peroral or intravenous. In general it has proved advantageous in the case of intraveneous administration, to administer about 0.01 to 10 mg/kg, preferably 0.1 to 5 mg/kg bodyweight per day, and, in the case of peroral administration to administer about 0.05 to 20 mg/kg, preferably 0.5 to 50 mg/kg bodyweight per day to achieve effective results.

The following Examples illustrate processes for the production of compounds according to the present invention.

EXAMPLE 1

2,6-Dimethyl-4-[1-(3-methoxyphenyl)-ethyl]-1,4-dihydropyridine-3,5-dicarboxylic acid dimethyl ester.

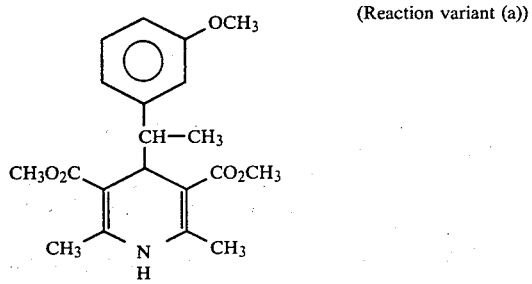

(Reaction variant (a))

16.4 g of 2-(3-methoxyphenyl)-propionaldehyde, 23.2 g of methyl acetoacetate and 2.1 ml of $NH_3$ (33% strength) in 50 $cm^3$ of ethanol were heated under reflux for 4 hours. After the mixture had cooled, the product crystallised out. It was purified by recrystallisation from ethanol.

Yield: 26.7 g (75%).
Melting point: 145° to 147° C.

The following compounds of the present invention were obtained analogously: 2,6-dimethyl-4-[1-(3-methoxyphenyl)-ethyl]-1,4-dihydropyridine-3,5-dicarboxylic acid diisopropyl ester, 2,6-dimethyl-4-[1-(3-methoxyphenyl)-ethyl]-1,4-dihydropyridine-3,5-dicarboxylic acid dibutyl ester, 2,6-dimethyl-4-[1-(2-chlorophenyl)-ethyl]-1,4-dihydropyridine-3,5-dicarboxylic acid diethyl ester, 2,6-dimethyl-4-[1-(2-chlorophenyl)-ethyl]-1,4-dihydropyridine-3,5-dicarboxylic acid dipropyl ester and 2,6-dimethyl-4-[1-(3-nitrophenyl)-ethyl]-1,4-dihydropyridine-3,5-dicarboxylic acid dimethyl ester.

EXAMPLE 2

2,6-Dimethyl-4-(2'-chlorophenylmethyl)-1,4-dihydropyridine-3,5-dicarboxylic acid dimethyl ester

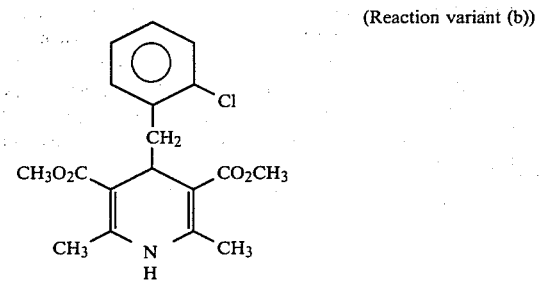

(Reaction variant (b))

15.4 g of 2-chlorophenylacetaldehyde and 23 g of methyl β-aminocrotonate in 50 ml of ethanol were heated under reflux for 4 hours. After the mixture had cooled, the product precipitated. It was recrystallized from methanol.

Yield: 21 g (60%).
Melting point: 178° C. to 179° C.

The following compounds of the present invention were obtained analogously: 2,6-dimethyl-4-(2'-chlorophenyl)-methyl-1,4-dihydropyridine-3,5-dicarboxylic acid diisopropyl ester, 2,6-dimethyl-4-(3',4'-dimethoxyphenyl)-methyl-1,4-dihydropyridine-3,5-dicarboxylic acid dimethyl ester and 2,6-dimethyl-4-(3',4'-dimethoxyphenyl)-methyl-1,4-dihydropyridine-3,5-dicarboxylic acid dipropyl ester.

EXAMPLE 3

2,6-Dimethyl-4-(4'-methoxyphenylmethyl)-1,4-dihydropyridine-3,5-dicarboxylic acid 3-methyl ester 5-isopropyl ester.

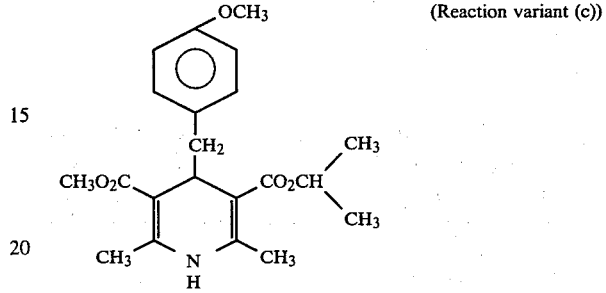

(Reaction variant (c))

24.8 g of 2-(4'-methoxyphenyl)-ethylideneacetoacetic acid methyl ester and 14.3 g of isopropyl β-aminocrotonate in 100 $cm^3$ of ethanol were heated under reflux for 4 hours. When the mixture had cooled, the product was filtered off and recrystallised from ethanol.

Yield: 18.6 g (50%).
Melting point: 163° C. to 165° C.

The following compound of the present invention was obtained analogously: 2,6-dimethyl-4-(3',4'-dimethoxyphenylmethyl)-1,4-dihydropyridine-3,5-dicarboxylic acid 3-ethyl ester 5-isopropyl ester.

EXAMPLE 4

2,6-Dimethyl-4-diphenylmethyl-1,4-dihydropyridine-3,5-dicarboxylic acid diethyl ester

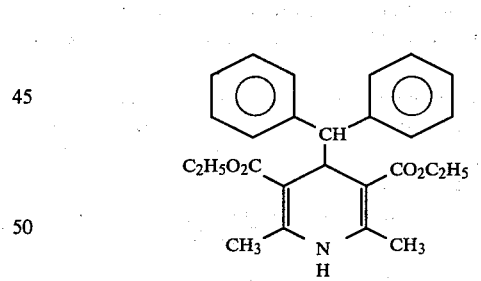

(Reaction variant (b))

9.6 g of diphenylacetaldehyde and 26 g of ethyl β-aminocrotonate in 50 $cm^3$ of ethanol were heated under reflux for 8 hours. After the mixture had cooled, the product precipitated. It was washed with ether and recrystallised from ethanol.

Yield: 10.4 g (25%).
Melting point: 140° C.

EXAMPLE 5

2,6-Dimethyl-4-(2',6'-dimethylphenoxymethyl)-1,4-dihydropyridine-3,5-dicarboxylic acid diethyl ester

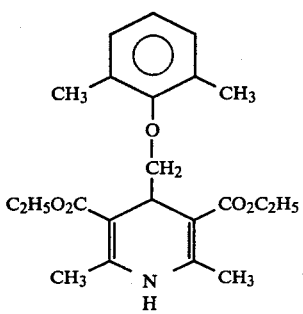

(Reaction variant (b))

16.4 g of 2,6-dimethylphenoxyacetaldehyde and 26 g of ethyl β-aminocrotonate in 50 cm³ of ethanol were heated under reflux for 4 hours. After the mixture had cooled, the product precipitated, and was recrystallised from ethanol.

Yield: 31.3% (55%).

Melting point: 106° C. to 107° C.

The following compound of the present invention was obtained analogously: 2,6-dimethyl-4-(2',6'-dichlorophenoxymethyl)-1,4-dihydropyridine-3,5-dicarboxylic acid dimethyl ester.

Among the new 1,4-dihydropyridine salts of the invention, those salts (especially acid-addition salts) that are pharmaceutically acceptable are particularly important and are preferred.

The new free 1,4-dihydropyridines of the general formula (I) and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound which is a 1,4-dihydropyridine of the formula

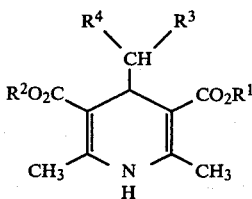

or a salt pharmaceutically acceptable thereof, in which

R¹ and R² are identical or different and denote a straight-chain or branched alkyl radical with 1 to 4 carbon atoms, R³ represents a hydrogen atom, a methyl group or a phenyl radical and R⁴ represents a phenyl or phenoxy radical unsubstituted, or may optionally carry 1 substituent selected from nitro, halogen, methyl, methoxy or dimethyl, with a proviso that R³ represents hydrogen or methyl only when R⁴ is phenoxy or substituted phenoxy.

2. A compound according to claim 1 which is 2,6-Dimethyl-4-diphenylmethyl-1,4-dihydropyridine-3,5-dicarboxylic acid diethyl ester.

3. A compound according to claim 1 which is 2,6-Dimethyl-4-(2',6'-dimethylphenoxymethyl)-1,4-dihydropyridine-3,5-dicarboxylic acid diethyl ester.

4. A pharmaceutical composition containing as an active ingredient a circulation-influencing effective amount of a compound according to claim 1 in admixture with an inert pharmaceutical carrier.

5. A pharmaceutical composition according to claim 4 in the form of a sterile or physiologically isotonic aqueous solution.

6. A composition according to claim 4 or 5 containing from 0.5 to 95% by weight of the said active ingredient.

7. A medicament in dosage unit form comprising a circulation-influencing effective amount of a compound according to claim 1 together with an inert pharmaceutical carrier.

8. A medicament of claim 7 in the form of tablets, pills, dragees, capsules, ampoules, or suppositories.

9. A method of lowering blood pressure in warm-blooded animals which comprises administering to the animals in need of such treatment, a blood pressure lowering effective amount of an active compound according to claim 1 either alone or in admixture with a diluent or in the form of a medicament.

* * * * *